US008551730B2

(12) United States Patent
Azucena et al.

(10) Patent No.: US 8,551,730 B2
(45) Date of Patent: Oct. 8, 2013

(54) USE OF A REFERENCE SOURCE WITH ADAPTIVE OPTICS IN BIOLOGICAL MICROSCOPY

(75) Inventors: Oscar Azucena, Santa Cruz, CA (US); Joel Kubby, Santa Cruz, CA (US); Jian Cao, Stanford, CA (US); William Sullivan, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 585 days.

(21) Appl. No.: 12/605,325

(22) Filed: Oct. 24, 2009

(65) Prior Publication Data

US 2010/0105105 A1    Apr. 29, 2010

Related U.S. Application Data

(60) Provisional application No. 61/197,291, filed on Oct. 24, 2008.

(51) Int. Cl.
*G01N 1/30*    (2006.01)
(52) U.S. Cl.
USPC ........................................... 435/40.5
(58) Field of Classification Search
None
See application file for complete search history.

(56) References Cited

U.S. PATENT DOCUMENTS

| 6,165,720 | A  * | 12/2000 | Felgner et al. ............... 435/6.11 |
| 6,384,952 | B1   | 5/2002  | Clark |
| 6,570,143 | B1 * | 5/2003  | Neil et al. .................. 250/201.9 |
| 6,648,473 | B2   | 11/2003 | DellaVecchia |
| 6,771,417 | B1   | 8/2004  | Wolleschensky |
| 7,805,183 | B2 * | 9/2010  | Keely et al. .................. 600/476 |
| 2002/0154398 | A1 | 10/2002 | Wolleschensky |
| 2003/0230710 | A1 | 12/2003 | Wolleschensky |
| 2005/0244921 | A1* | 11/2005 | Tsien et al. .................. 435/69.1 |
| 2006/0033933 | A1 | 2/2006 | Feierabend |
| 2007/0253057 | A1 | 11/2007 | Potsaid |
| 2007/0268592 | A1 | 11/2007 | Kam |
| 2008/0007693 | A1 | 1/2008 | Williams |
| 2010/0298504 | A1* | 11/2010 | Janczewski et al. .......... 525/418 |

FOREIGN PATENT DOCUMENTS

EP    1123491 B    5/2002

OTHER PUBLICATIONS

Babcock, H.W., "The possibility of compensating astronomical seeing", Pub. Astron. Soc. Pac., 65:229-236 (1953).
Booth, M.J., "Adaptive Optics in Microscopy", Phil. Trans. R. Soc. A., Math. Phys. Eng. Sci., 365:2829-43 (2007).
Liang, J., Williams, D.R., Miller, D.T., "Supernatural vision and high-resolution retinal imaging through adaptive optics", J. Opt. Soc. Am. A14:2884-92 (1997).

* cited by examiner

*Primary Examiner* — N. Yang
*Assistant Examiner* — Richard Moerschell
(74) *Attorney, Agent, or Firm* — Adam Warwick Bell; Matthew Rupert Kaser; Jason A. Kanter

(57) ABSTRACT

Methods of microscopic imaging of biological tissue using adaptive optics technology to improve the image focus and sharpness. Wavefront measurements are taken by using a novel method of seeding biological tissue by using a fluorescent microsphere as a "guide star" as a natural point-source reference. The current methods are capable of improving the Strehl ratio of modern biological microscopes as much as 15 times.

11 Claims, 3 Drawing Sheets

USE OF A REFERENCE SOURCE WITH ADAPTIVE OPTICS IN BIOLOGICAL MICROSCOPY

RELATIONSHIP TO OTHER APPLICATIONS AND CLAIM OF PRIORITY

Figure 1:
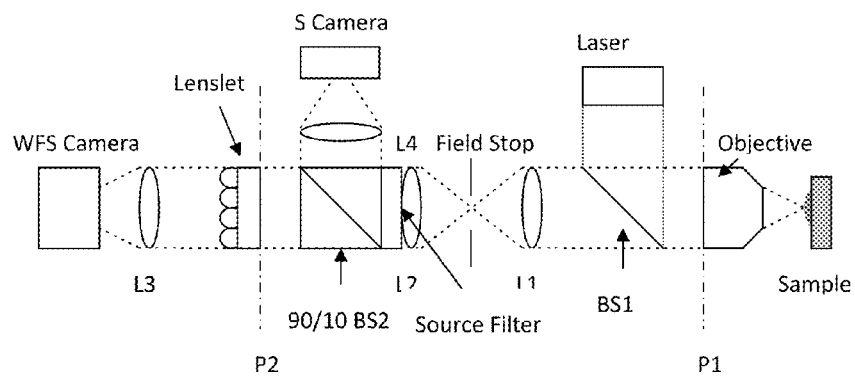

This application claims priority to and the benefit of U.S. provisional patent application No. 61/197,291 filed 24 Oct. 2009 entitled "Use of a reference source with adaptive optics in biological microscopy".

GOVERNMENT SUPPORT CLAUSE

This invention was made with government support under National Science Foundation Agreement Nos. 8976783 and PHY 0120999. The government has certain rights in the invention.

FIELD OF THE INVENTION

The invention relates to methods of microscopic imaging using adaptive optics technology to improve the Strehl ratio (and therefore image focus and sharpness) of microscopic imaging of biological tissue. Wavefront measurements are made by using a novel method of seeding biological tissue by using a fluorescent microsphere as a "guide star" as a natural point-source reference.

BACKGROUND

Changes in the index of refraction due to tissue composition limit the resolving power of biological microscopy [1-4]. This effect is more pronounced in deep tissue imaging where the light travels through many layers of cellular structures including cytoplasm and plasma membrane. Consequently, biological microscopy technology is not capable of obtaining high quality live images in unfixed samples more than 30 microns beneath the plasma membrane. Many important biological processes occur in deep tissue such as stem cell division, neurogenesis and the key developmental events following fertilization. A method that can be used to improve deep tissue imaging is Adaptive Optics (AO). AO is a technique used in telescopes to measure and correct the aberration introduced by the turbulence in the optical path [5, 6]. AO has also been applied to vision science to enhance our understanding of the human eye [7, 8]. Biological microscopy is limited by aberrations introduced when imaging through thick biological tissue. There is s need for a wavefront sensor to measure the wavefront error induced by biological tissue so as to improve the Strehl ratio of microscopes when imaging biological tissue.

BRIEF DESCRIPTION OF THE INVENTION

Optical aberrations are introduced during optical imaging through biological tissue. The invention encompasses methods of microscopy using adaptive optics technology to improve the Strehl ratio of microscopical imaging when imaging biological tissue.

The Strehl Ratio is usually defined at the best focus of the imaging system under study. The Strehl ratio is the ratio of the observed peak intensity at the detection plane of a telescope or other imaging system from a point source compared to the theoretical maximum peak intensity of a perfect imaging system working at the diffraction limit. This is closely related to the sharpness criteria for optics. The Strehl ratio is commonly used to assess the quality of a percieved image in the presence of atmospheric turbulence and assess the performance of any adaptive optical correction system.

The methods of the invention comprise a method for measuring optical aberrations introduced during optical imaging through biological tissue, the method comprising the steps of: the steps of: (i) seeding a medium with a reference source (the "guide star" reference), (ii) applying a biological tissue to the seeded medium, (iii) subjecting the biological tissue on the seeded medium to adaptive optics microscopy, and (iv) measuring the optical aberrations caused by imaging through the biological tissue using adaptive optics. In certain embodiments the method the reference source is fluorescent, and in certain embodiments may be a fluorescent microsphere. In various embodiments the reference source need not be a microsphere but may be any other source of fluorescent light such as dyes, particles, polymers etc impregnated with a fluorescent substance. For example the reference source may be a quantum dot, a bead, a dye, or a fluorescent protein (e.g., GFP, YFP etc.). In some embodiments the method of the invention uses a Shack-Hartmann wavefront sensor to measure the wavefront error induced during optical imaging through biological tissue. Any appropriate wavefront sensor could be used with the methods of the invention, and any suitable method for sensing and measuring the input wavefront could be used. For example the Hartman method could be used, although this is generally less accurate.

In the present disclosure, a Shack-Hartmann wavefront sensor was designed to measure the wavefront error induced by a *Drosophila* embryo. The *Drosophila* embryo is simply used as a convenient experimental example of a biological tissue and any biological tissue could be imaged using the methods of the invention.

The sequence of events as described above may vary and it in not necessary for the medium to be seeded first, and for the biological tissue to then be placed into the seeded medium. The biological tissue may be seeded directly or the biological tissue may be placed into the medium than then the medium and/or the tissue seeded with the fluorescent reference source. In an alternative embodiment the invention encompasses a method for measuring optical aberrations introduced during optical imaging through biological tissue, the method comprising the steps of: (i) providing a fluorescent reference source, (ii) seeding a biological tissue or a medium in which a biological tissue is present with the fluorescent reference source, (ii) subjecting the biological tissue on the seeded medium to adaptive optics microscopy, and (iv) measuring the optical aberrations caused by imaging through the biological tissue using adaptive optic microscopy. The fluorescent reference source may be selected from the group consisting of: a fluorescent microsphere, quantum dot, a fluorescent bead, a fluorescent dye, and a fluorescent protein.

The fluorescent reference source may be seeded into the biological tissue or the medium in which the biological tissue is present by physical distribution (sprinkling), or by soaking or injecting the biological tissue or the medium with the fluorescent reference source. In another embodiment, the fluorescent reference source is seeded into the biological tissue by genetic breeding and is inherently present in the biological tissue.

In another embodiment, the method uses two or more fluorescent reference sources to allow for tomographic measurements using adaptive optic microscopy, or multi-conjugate adaptive optics, or multi-object adaptive optics.

BRIEF DESCRIPTION OF THE FIGURES AND TABLES

FIG. 1. Microscope with a Shack-Hartmann wavefront sensor. BS1 allows the laser light to be focused onto the sample. BS2 allows for both the science camera and the WFS to simultaneously see the fluorescent microsphere.

Figure 2:
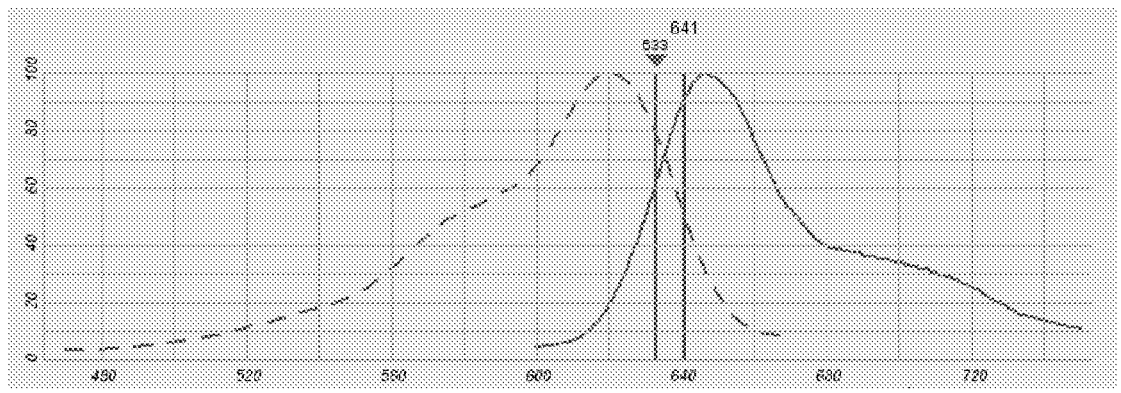

FIG. 2. Polystyrene microsphere optical absorption and emission curves. The absorption and emission curves are shown by the dashed and solid lines, respectively. The edge of the source filter is the red line. The emission filer has a 90% transmission for wavelengths greater then 641 nm.

Figure 3:
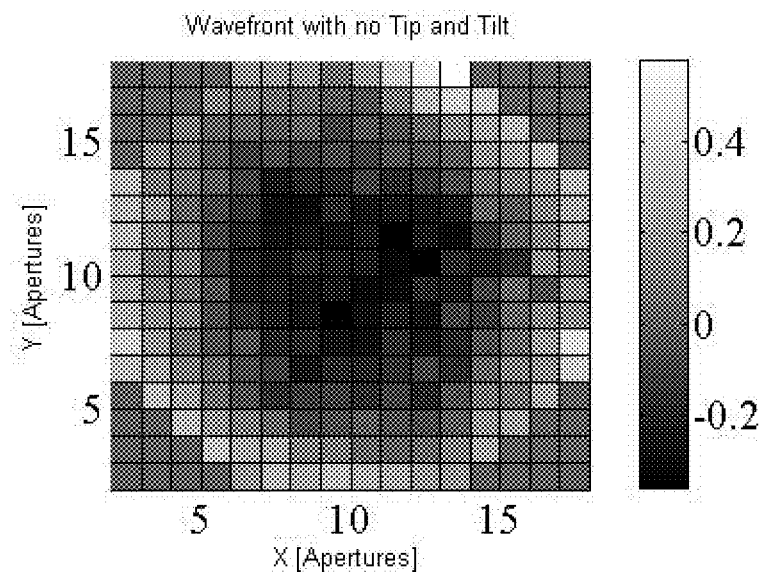

FIG. 3. 20× wavefront measurement with no tip and tilt. The x and y axis are scaled to the sub-aperture diameter. The legend is scale in microns.

Figure 4:
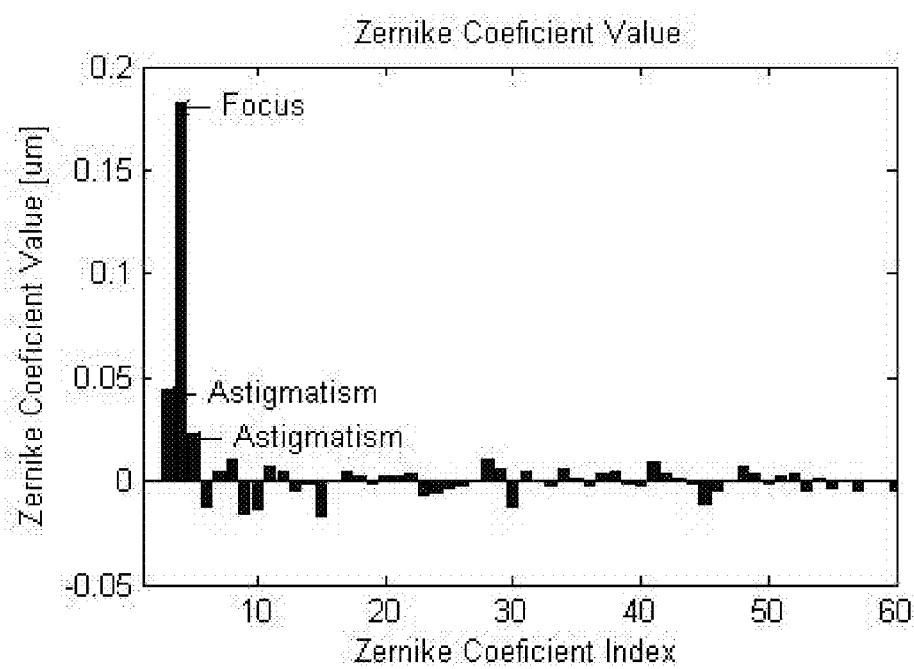

FIG. 4. Zernike Coefficient values for the wavefront shown in FIG. 3. Focus and Astigmatism are labeled.

Figure 5:
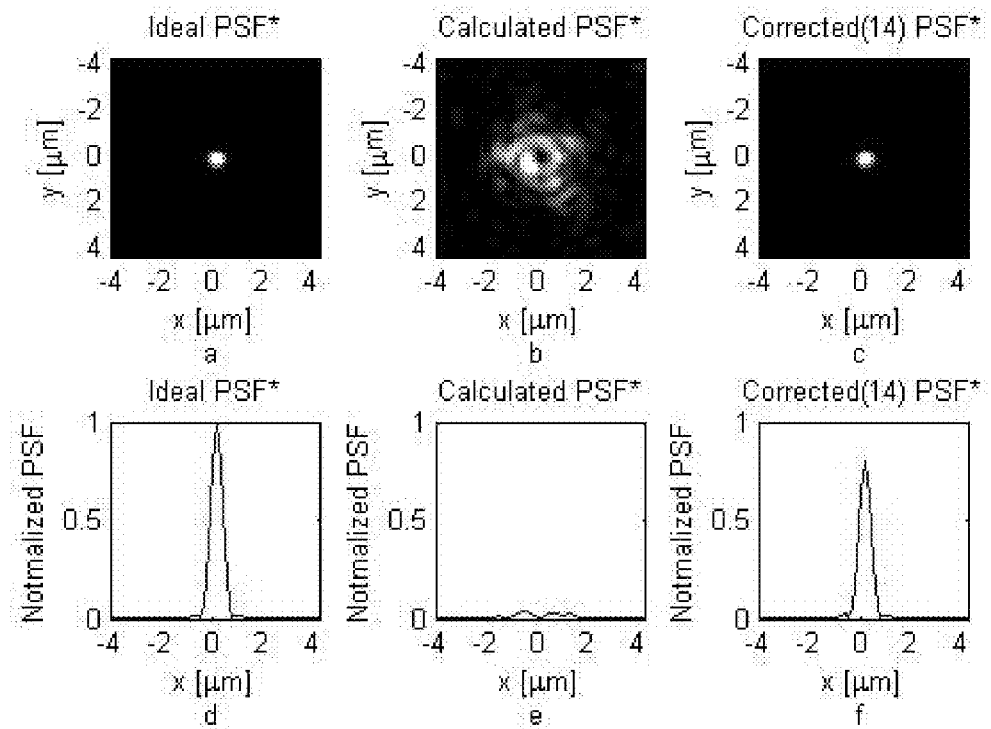

FIG. 5. PSF analysis, a) calculated using a flat wavefront, b) calculated using the wavefront in FIG. 3 (normalized to its maximum), c) calculated by removing the first 14 Zernike's of FIG. 3, d) cross-sectional view of a, e) cross-sectional view of b, f) cross-sectional view of c.

Figure 6:
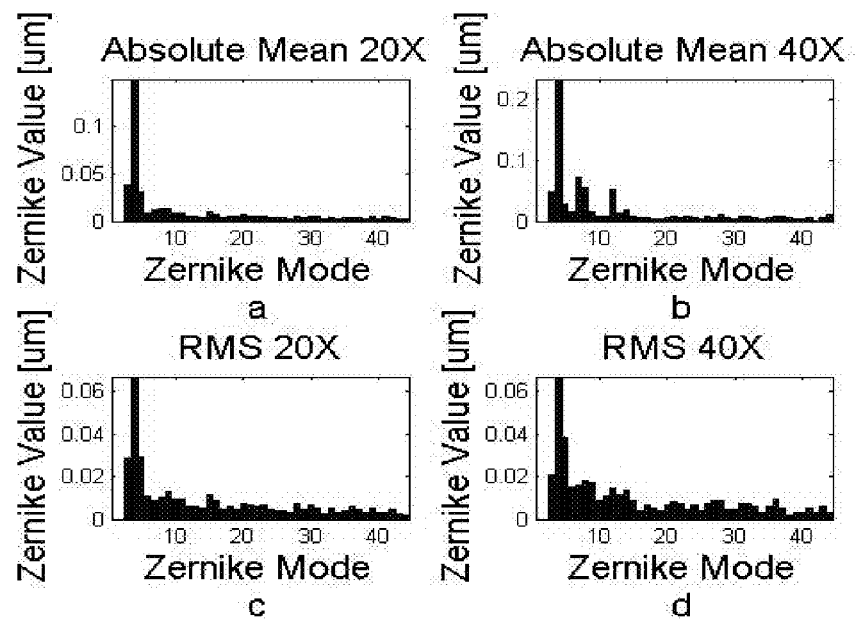

FIG. 6. Zernike statistical data for the measurement in Table 1. a and b) mean of the absolute value for each Zernike mode 20× and 40× respectively, c and d) room-mean-square value for each Zernike mode 20× and 40× respectively.

Table 1. Statistical data for 20× and 40× objectives. Peak-to-Valley (PV), Root-Mean-Square (RMS), Strehl (S), Strehl after correcting first 14 Zerniki's (S(14)), Strehl after correcting first 65 Zerniki's (S(65)).

Table 2. Isoplanatic angle measurements for the 40× objective.

GENERAL REPRESENTATIONS CONCERNING THE DISCLOSURE

The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features. This specification incorporates by reference all documents referred to herein and all documents filed concurrently with this specification or filed previously in connection with this application, including but not limited to such documents which are open to public inspection with this specification.

DETAILED DESCRIPTION OF THE INVENTION

Described are methods of microscopic imaging of biological tissue using adaptive optics technology to improve the image focus and sharpness. Wavefront measurements are taken by using a novel method of seeding biological tissue by using a fluorescent microsphere as a "guide star" as a natural point-source reference. The current methods are capable of improving the Strehl ratio of modern biological microscopes as much as 15 times.

The invention encompasses methods for measuring aberrations introduced during optical imaging through biological tissue and using adaptive optics technology to improve the Strehl ratio of microscopes when imaging biological tissue. The methods comprise seeding a medium with a reference source, applying a biological tissue to the seeded medium, subjecting the biological tissue on the seeded medium to adaptive optics microscopy, and determining the aberrations in light wavelength caused by imaging through the biological tissue. In one aspect of the invention, the reference source is fluorescent. In another aspect of the invention, the reference source is a fluorescent microsphere. In yet another aspect of the invention, the method uses a Shack-Hartmann wavefront sensor.

Changes in the index of refraction due to tissue composition limit the resolving power of biological microscopy [1-4]. This effect is more pronounced in deep tissue imaging where the light travels through many layers of cellular structures including cytoplasm and plasma membrane. Consequently, biological microscopy technology is not capable of obtaining high quality live images in unfixed samples more than 30 microns beneath the plasma membrane. Many important biological processes occur in deep tissue such as stem cell division, neurogenesis and the key developmental events following fertilization. A method that can be used to improve deep tissue imaging is Adaptive Optics (AO). AO is a technique used in telescopes to measure and correct the aberration introduced by the turbulence in the optical path [5, 6]. AO has also been applied to vision science to enhance our understanding of the human eye [7, 8].

The idea for using adaptive optics for microscopes is relatively new and a lot of work is still needed. Most adaptive optics microscopes systems so far have not directly measured the wavefront due to the complexity of adding a wavefront sensor in an optical system and the lack of a natural point-source reference such as the "guide-star" used in astronomy. Instead, most AO scanning microscopy systems have corrected the wavefront by optimizing a signal received at a photo-detector by using a hill-climbing algorithm [9]. While there is a lot of important research being done in AO microscopy, many of the AO systems are specific to each microscope and a universal method for measuring the wavefront (or the results of the correction algorithm) is not currently available. Booth described some of the difficulties associated with the utilization of a Shack-Hartmann wavefront sensor (SHWS) in AO microscopy [9]. Most of these difficulties can be overcome if a suitable fluorescent point source could be found.

In this patent application, we disclose a method for measuring the wavefront aberrations. In the present example aberrations induced by a *Drosophila* embryo are measured by using a Shack-Hartmann wavefront sensor wherein light is emitted from an imbedded fluorescent microsphere. The *Drosophila* embryo is well suited to analysis as it is approximately 200 µm in diameter, rich in cytoplasm and amenable to experimental manipulation. A Shack-Hartmann wavefront sensor was designed to measure the wavefront error induced by a *Drosophila* embryo. The wavefront measurements were taken by using a novel method of seeding an embryo with a fluorescent microsphere as a "guide star." The maximum wavefront error for a 40× objective was 1.9 µm and 0.3 µm for the peak-to-valley and root-mean-square respectively. The measurements also show that the isoplanatic half-width is approximately 19 µm resulting in a field of view of 38 µm in total. These measurements show that current adaptive optics technology is capable of improving the Strehl ratio of modern biological microscopes as much as 15 times.

Methods

FIG. 1 shows the design of the system used to measure the wavefront aberration introduced by the *drosophila* embryo. Two different objectives 20× and 40× (Melles Griot, Rochester, N.Y.) were used with a numerical aperture of 0.4 and 0.65 respectively. L1 and L2 are 65 mm focal length lenses that image the aperture of the objective onto the Hartmann sensor, P1 and P2 are conjugate planes. The field-stop between L1 and L2 blocks the light coming from other parts of the field of view, allowing only the light from the bead to pass. Note, the field-stop could be moved further down the system since it is only needed by the Hartmann sensor. The large distance between L1 and the aperture (P1) allows for the excitation laser (HeNe λ=632 nm) to be placed in this area. The laser is directed to the optical path via the 45° beam splitter BS1 (Semrock, Rochester, N.Y.). A source filter was also added after L2 to reduce the effect of scattered light by the embryo and allow for the Hartmann Sensor to only see the emission light. By using the 90/10 beam splitter the bead can be simultaneously imaged by the Hartmann sensor and the science camera. The lens L3 demagnifies the pupil by a factor 2 so that it can fit into the cooled camera (Roper Scientific, Acton, N.J.). See FIG. 1.

An important part of measuring an accurate wavefront is the reference source. Astronomical adaptive optics makes use of a laser to create an artificial guide star in the mesospheric sodium layer, 90 km above sea level that is bright enough to perform adequate wavefront measurements [6]. Powerful and expensive lasers are needed to do so but the end result is that the adaptive optics system can correct over a much larger portion of the sky relative to the use of "natural guide stars." The reference source used to measure the wavefront in our AO microscope setup is a crimson fluorescent microsphere that is 1 µm in diameter (Invitrogen, Carlsbad, Calif.) [10]. FIG. 2 shows the general absorption and emission curves of the crimson bead, as well as the excitation source at ~633 nm and the edge of the source filter at 641 nm (90% pass for wavelengths greater then 641 nm). See FIG. 2.

Embryos from the Oregon-R wild-type strain of *D. melanogaster* were collected for 2 hrs on grape juice agar plates at 22° C. These embryos were dechlorinated in a 50% bleach solution and transferred to a vial containing 1 mL of phosphate-buffered saline (PBS) and 1 mL of heptane. Embryos were left at the interface for 45 sec before addition of 2 mL of a formaldehyde solution consisting of 4 parts 37.5% formalin and 5 parts methanol-free 40% para-formaldehyde. These embryos were left in fixative for 25 min, at which time all fixative is removed and the embryos are hand devittelinized and stored in PBTA (1× PBS, 1% Bovine Serum Albumin (BSA), 0.05% Triton X-100, 0.02% Sodium Azide) [11].

Glass slides were prepared by adding three spacers of double-sided tape. Dilutions of fluorescent beads (1:5000 and 1:10000) were dropped onto the slide between spacers and allowed to dry for 10 min. Fixed embryos were rinsed in PBS and then covered in a glycerol-based mounting media (Vectashield, Vector Laboratories). Embryos were then transferred to the bead-covered areas of the slide followed by a coverslip, which was sealed with nail polish.

Results

A reference Hartmann sensor image was obtained to cancel the aberrations introduced by the optical set up. The reference image was taken by imaging a single fluorescent bead onto the Hartman sensor. The bead was dried onto a glass slide and imaged with no coverslip or mounting media. The image was processed to obtain the location of the Hartmann spots by using a cross-correlation centroiding algorithm [12]. For each wavefront measurement, a new Hartmann sensor image was acquired with the sample prepared as describe in the previous section. The new measurement was then processed to determine the displacement of the Hartmann spots (slope measurements) relative to the reference image described above. The slope measurements were finally processed to obtain the wavefront by using a Fast Fourier Transform (FFT) reconstruction algorithm [13]. For each measurement the peak-to-valley (PV) and the root-mean-square (RMS) wavefront errors were collected. The wavefront function was also expanded into Zernike's circle polynomials to determine the relative strength of the different modes [14]. The wavefront measurements were also used to analyze the point spread function (PSF) by taking the Fourier transform of the complex pupil function: See Equation 1.

$$PSF(x, y) = \frac{\left|FT\left\{P(x', y') * \exp\left(i\frac{2\pi}{\lambda}w(x', y')\right)\right\}\right|^2}{|FT\{P(x', y')\}|^2 \xi = 0, \eta = 0} \xi = \frac{x}{\lambda f},$$

$$\eta = \frac{y}{\lambda f}$$

Equation 1

Where P is one inside the pupil and zero everywhere else, x' and y' are the coordinates at the pupil plane, and ξ are η the spatial frequency in the transform domain, x and y are the coordinates at the image plane, w is the wavefront measurement, and λ is the wavelength at which the measurement were taken.

A measurement of the wavefront for a 20× objective with a numerical aperture of 0.4 and a limiting aperture of 5.9 mm is shown in FIG. 3. The distance between points is equal to the sub-aperture diameter $d_{LA}$. As can be seen from FIG. 6 the peak to valley wavefront error is ~0.95 µm and the RMS wavefront effort for this measurement was 0.16 µm. FIG. 4 shows the Zernike coefficient for the wavefront shown in FIG. 3. As can be seen from FIGS. 3 and 4, focus, astigmatism, and other spherical aberrations dominate the wavefront. This is mainly due to the index mismatches in the optical path as well as the curved body of the embryo, which mostly introduced lower-order aberrations. A reassuring sign shown in FIG. 4 is that the amplitude of the higher-order aberrations are decreasing and by correcting a finite number of Zernike modes the imaging qualities of the optical system will greatly improve. See FIGS. 3, 4 and 5.

Image "a" in FIG. 5 shows the PSF for an optical system with no aberrations. Image b in FIG. 5 displays the PSF calculated by using equation 1 and the wavefront in FIG. 3. The Strehl ratio is defined as the ratio of the peak intensity of the PSF relative to the peak intensity of diffraction limited PSF [14]. Image e in FIG. 5 shows that the Strehl is approximately 0.08. The effect of removing the first 14 Zernike's can be seen in image c and f in FIG. 5. Using this simulation we can estimate that correcting the first 14 Zernike's will improve the Strehl ratio to 0.72.

Table 1 shows the statistical data gathered from the measurements taken. Measurement 1-9 were taken with the 20× objective, measurement 10-15, in gray highlights, were taken with the 40× objective. The measurements show a maximum peak-to-valley (PV) wavefront error of 1.21 µm and 1.8 µm for the 20× and 40× respectively. The maximum RMS wavefront error was 0.24 µm and 0.3 µm for the 20× and 40× respectively. The higher PV and RMS measurement in the 40× objective are mainly due to the spherical aberrations introduced by the higher numerical aperture. Column four in Table 1 also shows the Strehl ratio obtained by finding the maximum of Equation 1 for each measurement. By removing different Zernike modes we can also calculate the effect of removing different amounts of wavefront error. Column five and six demonstrate the effect of removing the first 14 and 65 Zernike's modes from each measurement. The data shows that correcting a small number of modes improves the imaging capabilities of the system.

FIG. 6 shows the statistical data for each Zernike mode for the measurements shown in Table 1. The data shows a gradual decrease in value with increasing Zernike mode. From this we can verify that spherical aberrations are the main source of wavefront error and the aberrations are higher in the 40× objective.

The isoplanatic angle is a relative measure of the field of view over which the AO system can operate and is mathematically defined as [6]:

$$\sigma_\theta^2 = \langle (\phi(X, 0) - \phi(X, \theta_0))^2 \rangle = 1 \text{ rad}^2 \qquad \text{Equation 2}$$

Where X is a vector representing the two dimensional coordinates, $\theta_0$ is the isoplanatic angle, and $\sigma_\theta^2$ is the mean-square error between the measured and observed wavefront. We can determine the isoplanatic half-width by multiplying the isoplanatic angle by the focal length of the objective.

In order to determine the isoplanatic angle we took wavefront measurements from two beads separated by some distance d. The two beads were excited separately by shining the laser on a single bead at a time. Table 2 shows three different measurements taken with a 40× objective. The first measurement shows that the wavefront error for the bead located at the center of the field of view RMS(1) is 0.98 radians, the wavefront error for the bead located 18 μm from the center is 1.24 radians, and the wavefront error between the two measurements is 0.77 radians. Taking the average of three measurements shows the isoplanatic half width is ~19 μm. See Table 2.

Discussion & Conclusions

One of the challenges in designing a SHWS is imposed by the amount of light the reference source can provide. Fluorescent microspheres are made out of fluorescent dye and the light emitted is proportional to the radius cubed, thus smaller beads provide less light. The size of the beads should be smaller than the diffraction limit of one sub-aperture of the Hartmann wavefront sensor. Note that this is larger than the diffraction limit of the microscope aperture by the ratio D (size of the aperture)/$d_{LA}$. Since the diffraction limit of microscope is inversely proportional to the numerical aperture (NA) smaller beads are needed for higher numerical aperture systems. Fortunately the light gathered by the objective also increases with increasing NA (light gathering power ~$NA^2$). Thus increasing the wavefront sampling by a factor of 4, increases the size of the microsphere radius by a factor of 2, and the amount of light emitted by a factor of 8. The only way to determine if a microsphere, or any fluorescent source, will work is to image it into a SHWS using the objective, as shown in FIG. 1. In order to increase the speed of the AO loop the bead size should be maximized.

An emerging field in adaptive optics is tomography AO, where multiple light sources together with multiple SHWS are used. The information from each wavefront sensor is then processed using a reconstructor to acquire a tomographic image of the index of refraction changes in the optical path. One of the advantages of using tomography AO is that it can provide information on the depth dependence on index of refraction variations in the tissue thus allowing for the AO system to correct for the wavefront aberrations only in the optical path. This technology can also extend the isoplanatic angle by correcting wavefront aberrations that are common to a larger field of view. By depositing multiple fluorescent beads into the biological sample and using multiple wavefront sensors we can also apply the tomographic techniques that have been developed for astronomical AO.

A Shack-Hartmann wavefront sensor was designed to measure the wavefront error induced by a *Drosophila* embryo. The wavefront measurements were taken by using a novel method of seeding an embryo with a fluorescent microsphere as a "guide star." The maximum wavefront error for a 40× objective was 1.9 μm and 0.3 μm for the Peak-to-Valley and Root-Mean-Square respectively. The measurements also show that the isoplanatic half width is approximately 19 μm resulting in a field of view of 38 μm in total. Analysis of the data demonstrated that current Adaptive Optics technology can improve the Strehl ratio of modern microscopes by 4 times on average, but improvement as high as 15 times were observed when imaging through 200 μm of tissue.

References

Van Helden, A., *The Invention of the Telescope*, Trans. Am. Phil. Soc. 67, no. 4., pp. 20-21 (1977).

A. Dunn, *Light scattering properties of cells*, Dissertation, University of Texas, Austin http://www.nmr.mgh.harvard.edu/~adunn/papers/dissertation/node7.html, 1998.

M. Schwertner, *Specimen-induced distortions in light microscopy*, J. Microscopy 228, pp. 97-102 (2007).

M. Schwertner, M. J. Booth, M. A. A. Neil & T. Wilson, *Measurement of specimen-induced aberrations of biological samples using a phase stepping interferometer*, 213, pp. 11-19 (2003).

Babcock, H. W., *The possibility of compensating astronomical seeing*, Pub. Astron. Soc. Pac., pp. 229-236 (1953).

Hardy, J. W., *Adaptive Optics for Astronomical Telescopes*, Oxford University Press, New York. 1998.

Liang J., B. Grim, S. Goelz, and J. F. Bille, *Objective measurement of wave aberrations of the human eye with the use of a Hartmann-Shack wavefront sensor*, J. Opt. Soc. of Am A, 11, pp. 1949-1957, (1994).

J. Liang, D. R. Williams, D. T. Miller, *Supernormal vision and high-resolution retinal imaging through adaptive optics*, J. Opt. Soc. Am. A14, pp. 2884-2892 (1997).

M. J. Booth, *Adaptive optics in microscopy*, Phil. Trans. A, Math Phys. Eng. Sci. 365, p. 2829-43 (2007).

D. Debarre, E. J. Botcherby, M. J. Booth, T. Wilson, *Adaptive optics for structured illumination microscopy*, Optic Express 16, No. 13, pp. 17137-17142 (2008).

P. N. Marsh, D. Burns, J. M. Girkin, *Practical implementation of adaptive optics in multiphoton microscopy*, Optic Express 11, No. 10, pp. 1123-1130 (2003).

M. Rueckel, J. A. Mack-Bucher, W. Denk, *Adaptive wavefront correction in two-photon microscopy using coherence-gated wavefront sensing*, Proc. Natl. Acad. Sci. 103, pp. 17137-17142 (2006).

J. L. Beverage, R. V. Shack, and M. R. Descour, *Measurement of the three-dimensional microscope point spread function using a Shack-Hartmann wavefront sensor*, J. Microscopy 205, pp. 61-75 (2002).

Invitrogen Corporation, *Fluorescence Spectra Viewer*, http://www.invitrogen.com/site/us/en/home/support/Research-Tools/Fluorescence-SpectraViewerseg.us.html, Last Accessed: Aug. 15, 2008.

J. Porter, H. Queener, J. Lin, K. Thorn, A. Awwal, *Adaptive Optics for Vision Science*, Wiley-Interscience, New Jersey, 2006.

S. Thomas, T. Fusco, A. Tokovinin, M. Nicolle, V. Michau and G. Rousset, *Comparison of centroid computation algorithms in a Shack-Hartmann sensor*, MNRAS 371, pp. 323-336 (2006).

S. Adkins, O. Azucena, J. Nelson, *The design and optimization of detectors for adaptive optics wavefront sensing*, SPIE 6272, p. 62721E (2006).

L. Poyneer, *Scene-based Shack-Hartmann wave front sensing: analysis and simulation*, Applied Optics 42(29), pp. 5807-5815 (2003).

D. L. Fried, *Least-square fitting a wave front distortion estimate to an array of phase-difference measurements*, J. Opt. Am. 67(3), pp. 370-375 (1977).

K. R. Freischlad, C. L. Koliopoulis, *Modal estimation of a wave front from difference measurements using the discrete Fourier transform*, J. Opt. Soc. Am. A, 3(11), pp. 1852-1861 (1986).

Lisa A. Poyneer, D. T. Gavel, J. M. Brase, *Fast wave-front reconstruction in large adaptive optics systems with use of the Fourier transform*, J. Opt. Soc. Am. A 19(10), pp. 2100-2111 (2003).

Don Gavel, Lab. for Adaptive Optics, University of California Santa Cruz, private communication (2008).

TABLE 1

| M | PV [um] | RMS [um] | S | S(14) | S(65) |
|---|---|---|---|---|---|
| 1 | 1.21 | 0.24 | 0.03 | 0.60 | 0.71 |
| 2 | 0.75 | 0.12 | 0.13 | 0.67 | 0.77 |
| 3 | 0.99 | 0.19 | 0.05 | 0.67 | 0.75 |
| 4 | 0.42 | 0.08 | 0.41 | 0.80 | 0.84 |
| 5 | 0.94 | 0.15 | 0.10 | 0.65 | 0.74 |
| 6 | 0.78 | 0.10 | 0.23 | 0.73 | 0.80 |
| 7 | 0.91 | 0.16 | 0.11 | 0.60 | 0.70 |
| 8 | 0.95 | 0.16 | 0.08 | 0.72 | 0.80 |
| 9 | 0.41 | 0.07 | 0.47 | 0.81 | 0.89 |
| 10 | 0.94 | 0.15 | 0.26 | 0.62 | 0.70 |
| 11 | 1.16 | 0.21 | 0.13 | 0.66 | 0.73 |
| 12 | 1.31 | 0.23 | 0.18 | 0.59 | 0.68 |
| 13 | 1.80 | 0.30 | 0.06 | 0.27 | 0.49 |
| 14 | 1.60 | 0.29 | 0.10 | 0.45 | 0.57 |
| 15 | 1.65 | 0.23 | 0.16 | 0.44 | 0.60 |
| mean | 1.05 | 0.18 | 0.17 | 0.62 | 0.72 |

TABLE 2

| Measurement | Distance [μm] | Angle [arcmin] | RMS(1) [rads] | RMS(2) [rads] | RMS(1-2) [rads] |
|---|---|---|---|---|---|
| 1 | 18 | 13.8 | 0.98 | 1.24 | 0.77 |
| 2 | 25 | 19.1 | 1.69 | 1.1 | 1.3 |
| 3 | 14 | 10.7 | 1.6 | 1.9 | 0.73 |
| Mean | 19 | 14.5 | 1.42 | 1.41 | 0.93 |

The invention claimed is:

1. A method for measuring optical aberrations introduced during optical imaging through biological tissue, the method comprising the steps of: (i) seeding a medium with two or more fluorescent sources for use as reference sources for adaptive optics tomography, (ii) applying a biological tissue to the seeded medium, (iii) subjecting the biological tissue on the seeded medium to adaptive optics tomography, and (iv) measuring the optical aberrations caused by imaging through the biological tissue using adaptive optics tomography, wherein optical aberrations are measured using multiple Shack-Hartmann wavefront sensors.

2. The method of claim 1 wherein the two or more fluorescent sources comprise the fluorescent proteins GFP and YFP.

3. The method of claim 1 wherein the fluorescent source is selected from the group consisting of: a fluorescent microsphere, quantum dot, a fluorescent bead, a fluorescent dye, and a fluorescent protein.

4. The method of claim 1 wherein the adaptive optics microscopy comprises tomography adaptive optics, where multiple light sources together with multiple Shack-Hartmann wavefront sensors are used and wherein the information from each wavefront sensor is processed using a reconstructor to acquire a tomographic image of the index of refraction changes in the optical path thereby allowing for the adaptive optice system to correct for the wavefront aberrations only in the optical path.

5. The method of claim 1 wherein the wavefront sensor is a Shack-Hartmann wavefront sensor, and wherein the maximum wavefront error for a 40× objective is 1.9 μm and 0.3 μm for the peak-to-valley and root-mean-square respectively.

6. A method for measuring optical aberrations introduced during optical imaging through biological tissue, the method comprising the steps of: (i providing two or more fluorescent sources for use as reference sources for adaptive optics tomography, (ii) seeding a biological tissue with said two or more fluorescent sources, (ii) subjecting the biological tissue on the seeded medium to adaptive optics tomography, and (iv) measuring the optical aberrations caused by imaging through the biological tissue using adaptive optics tomography, wherein optical aberrations are measured using multiple Shack-Hartmann wavefront sensors.

7. The method of claim 6 wherein the fluorescent sources comprises at least GFP and YFP.

8. The method of claim 7 wherein the said adaptive optic microscopy comprises tomography adaptive optics, where multiple light sources together with multiple Shack-Hartmann wavefront sensors are used and wherein the information from each wavefront sensor is processed using a reconstructor to acquire a tomographic image of the index of refraction changes in the optical path thereby allowing for the adaptive optice system to correct for the wavefront aberrations only in the optical path.

9. The method of claim 5 wherein the isoplanatic half-width is approximately 19 μm resulting in a field of view of 38 μm in total.

10. The method of claim 6 wherein the fluorescent reference source is seeded into the biological tissue or the medium in which the biological tissue is present by soaking or injecting the biological tissue or the medium with the fluorescent reference source.

11. The method of claim 6 wherein the fluorescent reference source is seeded into the biological tissue by genetic breeding and is inherently present in the biological tissue.

* * * * *